(12) United States Patent
Quallich et al.

(10) Patent No.: US 7,038,061 B2
(45) Date of Patent: May 2, 2006

(54) CRYSTALLINE ANHYDROUS AND MONOHYDRATE BENZOATE SALTS OF (2'S,3S)-3-HYDROXY-N-(2-[N-METHYL-N-4-(N-PROPYLAMINO-CARBONYL) PHENYL]AMINO-2-PHENYL)-ETHYLPYRROLIDINE

(75) Inventors: George J. Quallich, North Stonington, CT (US); Michael J. Castaldi, Pawcatuck, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/421,209

(22) Filed: Apr. 23, 2003

(65) Prior Publication Data

US 2004/0235936 A1 Nov. 25, 2004

Related U.S. Application Data

(63) Continuation of application No. PCT/IB03/00560, filed on Feb. 17, 2003.

(51) Int. Cl.
*C07D 207/04* (2006.01)
(52) U.S. Cl. .................................... 548/550
(58) Field of Classification Search ................. 548/550
See application file for complete search history.

(56) References Cited

U.S. PATENT DOCUMENTS 6,201,007 B1 * 3/2001 Ito et al. .................... 514/422
6,294,557 B1 9/2001 Ito et al.

FOREIGN PATENT DOCUMENTS

WO 02088082 11/2002

OTHER PUBLICATIONS

Search Report, PCT/IB 03/00560, Apr. 10, 2003.

* cited by examiner

*Primary Examiner*—Kamal A. Saeed
(74) *Attorney, Agent, or Firm*—Steve T. Zelson; Jolene W. Appleman

(57) ABSTRACT

A process for preparing an anhydrous benzoate salt in crystalline form having the formula I:

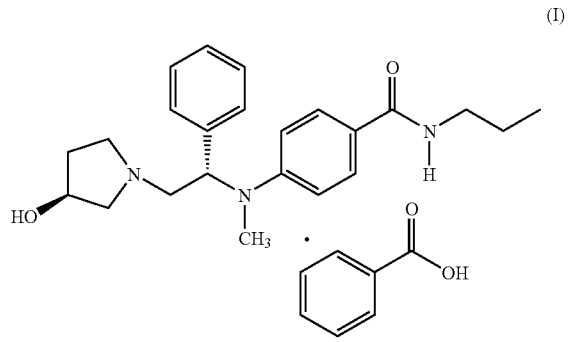

(I)

and the corresponding benzoate monohydrate in crystalline form. The benzoate salts and pharmaceutical compositions thereof are selective kappa-receptor agonists, and are useful as analgesics, anesthetics, anti-inflammatory or neuroprotective agents, or in the treatment of arthritis, stroke or functional bowel disease.

5 Claims, No Drawings

CRYSTALLINE ANHYDROUS AND MONOHYDRATE BENZOATE SALTS OF (2'S,3S)-3-HYDROXY-N-(2-[N-METHYL-N-4-(N-PROPYLAMINO-CARBONYL)PHENYL] AMINO-2-PHENYL)-ETHYLPYRROLIDINE

This application claims priority under 35 U.S.C. 120 of International Application No. PCT /IB03/00560, filed Feb. 17, 2003, entitled Crystalline Anhydrous and Monohydrate Benzoate Salts of (2'S,3S)-3-Hydroxy-N-{2-[N-methyl-N-4-(N-propylamino-carbonyl)phenyl]amino-2-phenyl}-Ethylpyrrolidine, naming Pfizer Products Inc, George Joseph Quallich, and Michael James Castaldi as applicants; and designating the United States.

FIELD OF THE INVENTION

This invention relates to crystalline anhydrous and monohydrate benzoate salts of (2'S,3S)-3-hydroxy-N-{2-[N-methyl-N-4-(N-propylamino-carbonyl)phenyl]amino-2-phenyl}-ethylpyrrolidine, processes for preparing and using them. The pharmaceutically active salts of this invention have advantageous properties in formulations as selective kappa-receptor agonists.

BACKGROUND OF THE INVENTION

Opioid analgesics such as morphine are therapeutically useful, but their usage is strictly limited because of their side effects such as drug dependency and abuse. Thus, analgesics, with high effectiveness and reduced tendency in causing drug dependency, are desired. Considerable pharmacological and biochemical studies have been carried out to discover opioid peptides and opioid receptors. The discovery of the subtype of opioid receptor such as mu (μ), delta (δ), kappa (κ) in a variety of species, including human, has provided a beginning towards creating new analgesics. As a result of the belief that opioid analgesics such as morphine act as mu-receptor agonists, separating the action based on a kappa-receptor agonist from the action based on mu-receptor agonist has been investigated. Recently such kappa-selective agonists (kappa-agonists) have been reported from the above viewpoint for example, EMD-61753: A. Barber et al., *Br. J. Pharmacol.*, Vol. 113, pp. 1317–1327, 1994. Some of the kappa agonists actually have been studied in clinical trials (*Med. Res. Rev.*, Vol.12, p. 525, 1992).

U.S. Pat. Nos. 6,201,007 and 6,031,114 relate to certain pyrrolidinyl and pyrrolinyl ethylamine compounds and the salts thereof. These compounds are useful as kappa agonists, and have specific utilities as analgesic, anesthetic, anti-inflammatory or neuroprotective agents. The disclosure of each of the foregoing United States patents is incorporated herein in its entirety by reference.

Additionally, European Patent No. EP 0254545 B1 discloses a variety of ethylenediamine compounds which are related to the salts prepared by the present method. European Patent No. EP 0483580 B1 also discloses a variety of pyrrolidine compounds useful as analgesics, and International Patent Publication WO 96/30339, published Oct. 3, 1996, refers to a wide variety of pyrrolidinyl hydroxamic acid compounds as selective kappa-receptor agonists.

It has now been found that the anhydrous benzoic acid salt of (2S,3S)-3-hydroxy-N-{2-[N-methyl-N-4-(N-propylamino-carbonyl)phenyl]amino-2-phen-yl}-ethylpyrrolidine can be isolated in a crystalline form which has advantageous physical chemical properties which improve the ease of preparing a purified drug. In addition, it has been determined that the process of the present invention permits the formation of the monohydrate benzoic acid salt in a highly pure, crystalline form which is sufficiently stable, chemically and physically, to meet the requirements for preparing a clinically useful drug formulation.

SUMMARY OF THE INVENTION

The present invention comprises a process of preparing an anhydrous benzoate salt in crystalline form having the formula I:

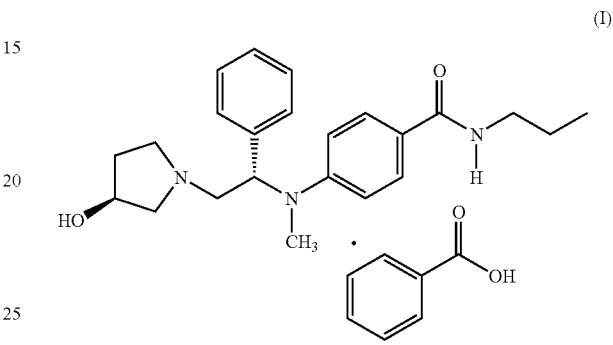

which process comprises (a) treating a compound having the formula II:

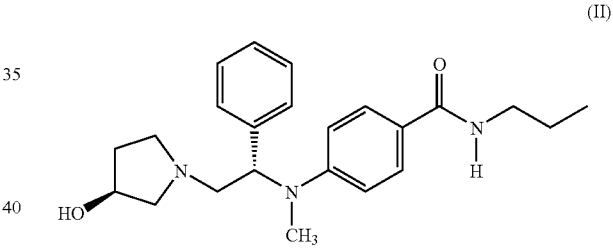

with benzoic acid in the presence of an alkyl alcohol, and (b) isolating the anhydrous salt of formula I in crystalline form.

The invention also comprises a process of preparing a benzoate monohydrate salt, in crystalline form, having the formula III:

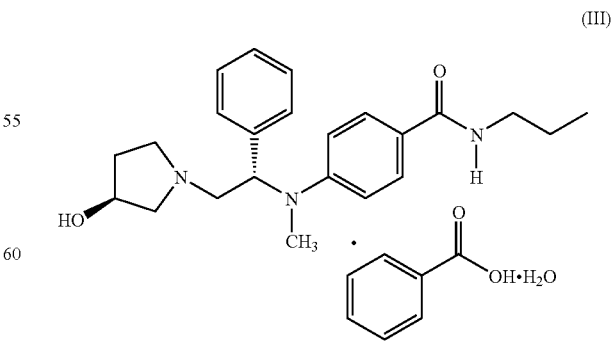

which process comprises (a) treating an anhydrous benzoate salt having the formula I:

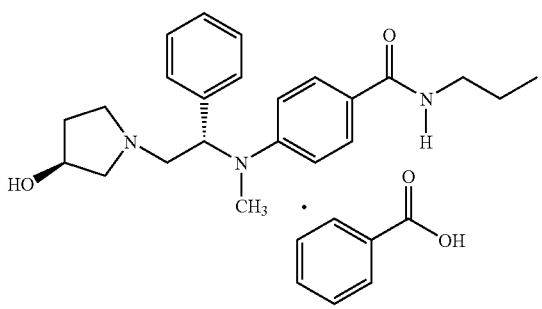

(I)

with water in the presence of an alkyl alcohol, and (b) isolating the benzoate monohydrate salt of formula III in crystalline form.

The invention further comprises an anhydrous benzoate salt having the formula I:

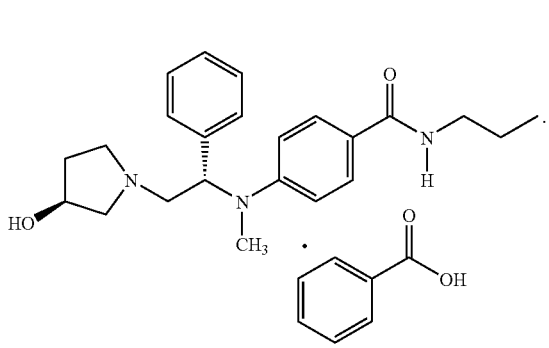

(I)

In a particular aspect, the invention provides the anhydrous benzoate salt having a powder X-ray diffraction pattern obtained using copper K-alpha1 radiation (X=1.5046 Å) which shows main peaks at 9.95, 10.85, 11.4, 13.5, 14.8, 15.8, 17.4, 18.6, 19.6, 20.0, 21.25, 22.0, 22.6, 24.0, 25.45, 27.4, 29.0, 30.45, 31.0, and 31.8.

The invention additionally comprises a benzoate monohydrate salt of formula III:

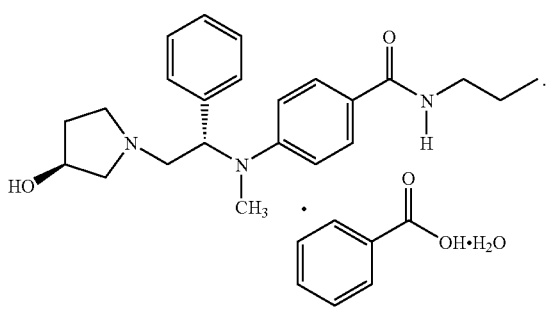

(III)

In a particular aspect, the invention comprises the benzoate monohydrate salt characterized in having a powder X-ray diffraction pattern obtained using copper K-alpha, radiation (X=1.5046 Å) which shows main peaks at 6.55, 8.0, 11.3, 12.0, 13.1, 14.6, 16.0, 17.8, 18.45, 20.0, 20.8, 22.0, 23.1, 24.4, 24.5, 25.5, 26.3, 27.45, 28.4, 29.5, 30.0, 31.5, 33.7, 34.5, and 35.8.

Furthermore, the invention comprises a pharmaceutical composition for the treatment of a medical condition for which agonist activity toward opioid kappa receptor is needed, in a mammalian subject, which comprises a therapeutically effective amount of the anhydrous or monohydrate benzoic acid salt set forth herein, and a pharmaceutically inert carrier. The invention also provides a pharmaceutical composition comprising the anhydrous or monohydrate set forth herein, which is useful as an analgesic, anesthetic, anti-inflammatory or neuroprotective agent, or useful in the treatment of arthritis, stroke or functional bowel disease.

The present invention further comprises a method for the treatment of a medical condition for which agonist activity toward opioid kappa receptor is needed, in a mammalian subject, which comprises administering to said subject a therapeutically effective amount of the anhydrous or monohydrate benzoic acid salt described herein. The present invention also comprises a method for the treatment of a medical condition for which analgesia, anesthesia, anti-inflammatory action or neuroprotection is needed, or for the treatment of arthritis, stroke or functional bowel disease, in a mammal, which comprises administering to said mammal a therapeutically effective amount of the anhydrous or monohydrate benzoic acid salt described herein.

DETAILED DESCRIPTION OF THE INVENTION

The kappa agonist benzoate salts (kappa-receptor agonists) of this invention having formulas I and III can be prepared from the corresponding free base compound (2'S, 3S)-3-hydroxy-N-{2-[N-methyl-N-4-(N-propylamino-carbonyl)phenyl]amino-2-phenyl}-ethylpyrrolidine (II), which is described in U.S. Pat. No. 6,201,007, the contents of which are incorporated herein by reference.

The methods of the present invention are readily carried out. Thus, in the process of preparing the anhydrous benzoate salt of formula I, the free base compound (2'S,3S)-3-hydroxy-N-{2-[N-methyl-N-4-(N-propylaminocarb-onyl)phenyl]amino-2-phenyl}-ethylpyrrolidine is (a) treated with benzoic acid in the presence of an alkyl alcohol, and then (b) the anhydrous salt of formula I is isolated in crystalline form. The alkyl alcohol which is used in the process is selected from methyl alcohol, ethyl alcohol, isopropanol and sec-butanol, and the like, but preferably is isopropanol. In one aspect of the invention, the compound having the formula II is preliminarily dissolved in the alkyl alcohol prior to treatment with benzoic acid. Advantageously, the process of the invention may further comprise heating the solution of the compound having the formula II to between about 30° C. and about 60° C., but preferably, to about 40° C., prior to treatment with benzoic acid or a solution thereof. The solution of benzoic acid may be kept at ambient temperatures, or it is heated to between about 30° C. and about 60° C. Preferably, the solution of benzoic acid is heated to about 40° C. The isolation step may be carried out using any method known in the art, including filtration or centrifugation.

In another aspect of the invention, the benzoic acid is preliminarily dissolved in the alkyl alcohol prior to treating the compound having formula II. In yet another aspect, the process of the invention may further comprise heating the solution of benzoic acid to between about 30° C. and about 60° C. prior to treating the compound having formula II. In a particular aspect, the process may be carried out wherein the solution of benzoic acid is heated to about 40° C.

In the process of preparing the benzoate monohydrate salt of formula III, the anhydrous benzoate salt of formula I is (a) treated with water in the presence of an alkyl alcohol, and then (b) the benzoate monohydrate salt of formula III is isolated in crystalline form. The temperature at which the hydration process is carried out is not critical, and is conveniently carried out at ambient temperatures, thereby avoiding the energy costs of either heating or cooling. The co-solvent alkyl alcohol used in the process is selected from methyl alcohol, ethyl alcohol, isopropanol and sec-butanol, and the like, but preferably is isopropanol. In a typical embodiment of the process, the anhydrous benzoate salt having the formula I is preliminarily dissolved, slurried or suspended in the alkyl alcohol prior to treatment with water. The isolation step may be carried out using any method known in the art, including filtration or centrifugation.

The anhydrous and monohydrate benzoate salts prepared in accordance with the process of the present invention exhibit good kappa-receptor agonist activity, and thus are useful as analgesic, anesthetic, anti-inflammatory or neuroprotective agents, and are also useful in the treatment of arthritis, stroke, or abdominal pain, in a mammalian subject, especially a human. Specifically, these anhydrous and monohydrate benzoate salts are useful as analgesic agents for acute and chronic pain. Also, the anhydrous and monohydrate benzoate salts of the invention are useful as analgesic agents for treating peripheral mediated inflammatory pain caused, for example, by burns (induced by a contact with heat, acid or the other agents), scald (induced by a contact by hot liquid or steam), rheumatism and the like, in a mammal.

The salts prepared by the process of the present invention are also useful for the treatment of a medical condition for which agonist activity toward opioid kappa receptor is needed, in a mammal, which comprises administering to said mammal a therapeutically effective amount of the anhydrous or monohydrate benzoate salts.

The benzoate salts prepared by the processes of the present invention exhibit significant agonist activity toward opioid kappa-receptor and are thus useful as an analgesic, anesthetic, anti-inflammatory agent or neuroprotective agent, and also useful in the treatment of arthritis, stroke or functional bowel disease such as abdominal pain, for the treatment of a mammalian subject, especially a human subject.

The activity of the anhydrous and monohydrate benzoate salts prepared by the process of the present invention is demonstrated by the opioid receptor binding activity. Such activity may be determined in homogenate from guinea pig whole brain, as described by Regina, A., et al., in *J. Receptor Res.*, Vol. 12, pp. 171–180 (1992). In summary, tissue homogenate is incubated at 25° C. for 30 min in the presence of labelled ligand and test compounds. The mu-sites are labelled by 1 nM of (3H)-[D-Ala2,MePhe4,Gly-ol5]enkephalin (DAMGO), the delta-sites by 1 nM of (3H)-[D-Pen2,5]enkephalin (DPDPE) and the kappa-sites by 0.5 nM (3H)-Cl-977. The non specific binding is measured by use of 1 μM Cl-977 (kappa), 1 μM (DAMGO) (mu), 1 μM (DPDPE) (delta). Data are expressed as the $IC_{50}$ values obtained by a non-linear fitting program using the Cheng and Prusoff equation. An $IC_{50}$ value against kappa receptor for a potent salt is in the range of 0.01 to 100 nM.

The analgesic activity in the central nervous system of the kappa-agonist compounds prepared by the process of the present invention can also be demonstrated by the Formalin Test as described by Wheeler-Aceto, H., et al., in *Psychopharmacology*, Vol. 104, pp. 35–44 (1991). In this testing, male SD rats (80–100 g) are injected s.c. with a test compound dissolved in 0.1% methyl cellulose saline or vehicle. After 30 min, 50 μl of a 2% formalin are injected into a hind paw. The number of lickings of the injected paw, per observation period, is measured 15–30 min after the injection of formalin, and is expressed as % inhibition compared to the respective vehicle group. An $ED_{50}$ value for a potent salt prepared by the processes of this invention is less than 25 mg/kg p.o.

The activity of the kappa agonist salts prepared as disclosed herein against peripheral acute-pain can be demonstrated by the Randall-Selitto assay (M. E. Planas, *Pain*, Vol. 60, pp. 67–71 (1995)). In this testing, male SD rats (100–120 g) were used and the nociceptive threshold at the right paw was measured by Randall-Selitto (Ugo Basile) method. After three days of acclimation of assay condition, experiments were carried out. Hyperalgesia was induced by the intraplantar injection of a 0.1 ml/right paw of 1% solution of carrageenan. Painful pressure were delivered to the right plantar via a wedge-shaped piston and the level of response were measured at 3.5 and 4.5 hr later the carrageenan injection. Salts prepared in the working Examples as described below are tested in accordance with the above procedures. A good activity against acute pain is indicated by an $ED_{50}$ value which is less than 10 mg/kg p.o.

The activity of the kappa agonist salts disclosed herein against chronic pain at the periphery can be demonstrated by the adjuvant-induced hyperalgesia, according to the procedure described by Judith S. Waker, et al., as reported in *Life Sciences*, Vol. 57, pp. 371–378 (1995). In this testing, male SD rats weighing 180–230 g at the time of inoculation are used. To produce adjuvant arthritis, rats are anesthetized with ether and inoculated intradermally into the footpad of the right hindpaw with 0.05 ml of *Mycobacterium butyricum* suspended in paraffin oil (2 mg/ml). Nociceptive threshold is evaluated by paw pressure test, using the same procedures of the Randall-Selitto assay (as described above), and edema is measured as the width of foot. Assays are done through the whole period.

The sedation function of kappa agonist salts prepared by the process of the invention can be determined by the Rotarod Test as described by Hayes, A. G., et al., in *Br. J. Pharmacol.*, Vol. 79, pp. 731–736 (1983). In this testing, a group of 6–10 male SD rats (100–120 g) are selected for their ability of balancing on a rotating rod (diameter 9 cm, rate of rotation 5 r.p.m.). The selected rats are then injected s.c. with a test compound dissolved in 0.1% methyl cellulose saline. The animals are tested again 30 min after treatment; a rat falling off the bar more than twice within 150 seconds is considered to be showing motor impairment and the animal's performance (i.e., time on the rotarod) is recorded. The $ED_{50}$ value is defined as the dose of the drug which has the performance time observed in the control group. Salts prepared in the working Examples as described below are tested in accordance with the above procedures.

The diuresis function of the kappa agonists can be determined according to the procedure described by A. Barber, et al., *Br. J. Pharmacol.*, Vol. 111, pp. 843–851 (1994). Salts prepared in the working Examples as described below are tested in accordance with this procedure.

The kappa agonist benzoate salts prepared by the process of the present invention can be administered via either the oral, parenteral or topical routes to mammals. A preferable dosage level may be in a range of from 0.01 mg to 10 mg per kg of body weight per day, although variations will necessarily occur depending upon the weight and condition of the subject being treated, the disease state being treated and the particular route of administration chosen. However, a dosage level that is in the range of from 0.01 mg to 1 mg per kg of body weight per day, single or divided dosage is most desirably employed in humans for the treatment of pain in a postoperative patient and a pain like hyperalgesia caused by chronic diseases.

The salts prepared by the process of the present invention may be administered alone or in combination with pharmaceutically acceptable carriers or diluents by either of the above routes previously indicated, and such administration can be carried out in single or multiple doses. More particularly, these therapeutic agents can be administered in a wide variety of different dosage forms; i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective salts prepared by the process of the invention are present in such dosage forms at concentration levels ranging 0.5% to 7.0% by weight, preferably 1.0% to 5.0% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of the salt prepared by the process of the present invention in either sesame or peanut oil or in aqueous propylene glycol may be employed. The aqueous solutions should be suitably buffered (preferably between pH 4 to 8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the salts prepared by the process of the present invention topically when treating inflammatory conditions of the skin and this may preferably be done by way of creams, jellies, gels, pastes, ointments and the like, in accordance with standard pharmaceutical practice.

EXAMPLES

The present invention is illustrated by the following examples. However, it should be understood that the invention is not limited to the specific details of the examples.

Example 1

Anhydrous (2'S,3S)-3-Hydroxy-N{2-[N-methyl-N-4-(N-propylamino-carbonyl)phenyl]amino-2-phenyl}-ethylpyrrolidine Benzoate A clean, dry 22 L flask which was rinsed with isopropanol, and equipped with a paddle stirrer, was charged with 2,000 g (5.24 moles) of (2'S,3S)-3-hydroxy-N-{2-[N-methyl-N-4-(N-propylaminocarbonyl)phenyl]amino-2-phenyl}-ethylpyrrolidine and 10 L of isopropanol. The resulting solution was heated to 40° C., and filtered into a speck-free, isopropanol-rinsed 22 L flask equipped with a new paddle stirrer. Thereafter, a solution of 647 g (5.29 moles) of ACS reagent grade (99.9%) benzoic acid in 4 L of isopropanol was prepared. After heating to 40° C., the latter solution was filtered into the first solution, and the filter was then washed with 500 mL of isopropanol. The resulting amber solution was allowed to stir at room temperature overnight. In the morning, a white crystalline product was collected by filtration using a speck-free, isopropanol-rinsed filter. After drying at 45° C. under vacuum (with a nitrogen bleed) overnight, 2,180 g (82.9% yield) of (2'S,3S)-3-hydroxy-N-{2-[N-methyl-N-4(N-propylaminocarbonyl)phenyl]amino-2-phenyl}-ethylpyrrolidine benzoate was recovered. The powder X-ray diffraction pattern obtained using copper K-alpha radiation (X=1.5046 Å) shows main peaks at 9.95, 10.85, 11.4, 13.5, 14.8, 15.8, 17.4, 18.6, 19.6, 20.0, 21.25, 22.0, 22.6, 24.0, 25.45, 27.4, 29.0, 30.45,31.0, and 31.8.

Example 2

(2'S,3S)-3-Hydroxy-N-{2-[N-methyl-N-4-(N-propylaminocarbonyl)phen-yl]amino-2-phenyl}-ethylpyrrolidine Benzoate Monohydrate In a clean, dry 22 L flask which was rinsed with isopropanol, and equipped with a paddle stirrer, 499 g of anhydrous (2'S,3S)-3-hydroxy-N-{2-[N-methyl-N-4-(N-propylaminocarbonyl)phenyl]amino-2-phenyl}ethylpyrrolidine benzoate was dissolved with 2,640 mL of isopropanol. To this slurry was added 1,760 mL of filtered city water. The resulting pale yellow solution was stirred at room temperature, and after about two hours, a white slurry formed. Sixteen hours later, a white crystalline product was collected by filtration, and dried at 45° C. under vacuum (with a nitrogen bleed) overnight to afford 309 g (72% yield) of (2'S,3S)-3-hydroxy-N-{(2-[N-methyl-N-4-(N-propylaminocarbonyl)phenyl]amino-2-phenyl}-ethylpyrrolidine benzoate mono-hydrate. The powder X-ray diffraction pattern obtained using copper K-alpha radiation (X=1.5046 Å) shows main peaks at 6.55, 8.0, 11.3, 12.0, 13.1, 14.6, 16.0, 17.8, 18.45, 20.0, 20.8, 22.0, 23.1, 24.4, 24.5, 25.5, 26.3, 27.45, 28.4, 29.5, 30.0, 31.5, 33.7, 34.5, and 35.8. The monohydrate is also characterized by the single-crystal X-ray crystallographic parameters set forth in Table I.

TABLE I

A. Crystal Parameters

| | |
|---|---|
| Formula | $C_{23}H_{32}N_3O_2$ $^+C_7H_5O_2^-.H_2O$ |
| Crystallization Medium | Dichloromethane |

TABLE I-continued

| | |
|---|---|
| Crystal size, mm | 0.03 × 0.12 × 0.36 |
| Cell Dimensions | A = 11.258(2) Å |
| | B = 9.617(2) Å |
| | C = 13.4340(1) Å |
| | A = 90.0° |
| | B = 102.040(1)° |
| | Γ = 90.0° |
| | V = 1422.5(4) Å$^3$ |
| Space Group | P2$_1$ |
| Molecules/unit cell | 2 |
| Density, calc'd, g/cm$^3$ | 1.218 |
| Linear absorption factor, mm$^{-1}$ | 0.669 |
| B. Refinement Parameters | |
| Number of reflections | 1811 |
| Nonzero reflections (l > 3.0 σ) | 1477 |

What is claimed is:

1. A process for preparing an anhydrous benzoate salt in crystalline form having the formula I:

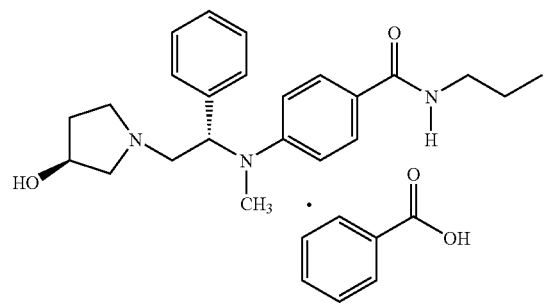

(I)

which comprises (a) treating a compound having the formula II:

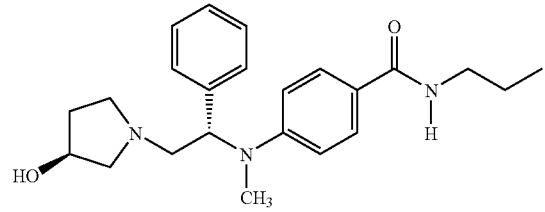

(II)

with benzoic acid in the presence of an alkyl alcohol, and (b) isolating the anhydrous salt of formula I in crystalline form.

2. The process of claim 1, wherein the compound having the formula II is preliminarily dissolved in the alkyl alcohol prior to said treating of the compound of formula I so as to form a solution; or wherein the alkyl alcohol is isopropanol.

3. The process of claim 1, wherein the benzoic acid is preliminarily dissolved in the alkyl alcohol prior to said treating of the compound having formula II so as to form a solution.

4. A process for preparing a benzoate monohydrate salt in crystalline form having the formula III:

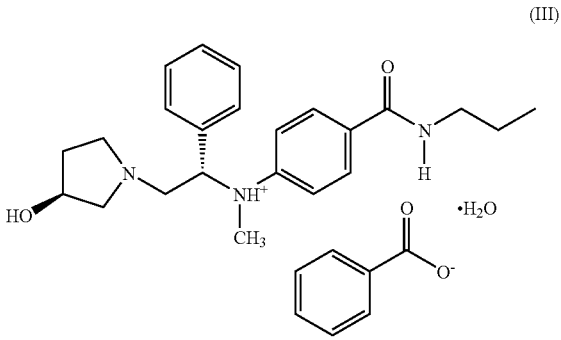

(III)

which comprises (a) treating an anhydrous benzoate salt having the formula I:

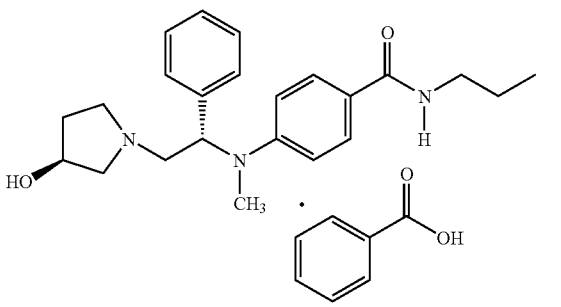

(I)

with water in the presence of an alkyl alcohol, and (b) isolating the benzoate monohydrate salt of formula III in crystalline form.

5. The process of claim 4, wherein the anhydrous benzoate salt having the formula I is preliminarily suspended in the alkyl alcohol prior to said treating said anhydrous benzoate; or wherein the alkyl alcohol is isopropanol.

* * * * *